(12) United States Patent
Duska-Mcewen et al.

(10) Patent No.: US 10,624,916 B2
(45) Date of Patent: Apr. 21, 2020

(54) NUTRITIONAL FORMULATIONS USING HUMAN MILK OLIGOSACCHARIDES FOR MODULATING INFLAMMATION

(71) Applicant: ABBOTT LABORATORIES, Abbott Park, IL (US)

(72) Inventors: Geralyn Duska-Mcewen, Columbus, OH (US); Sarah Comstock, East Lansing, MI (US); Sharon Donovan, Champaign, IL (US); Rachael Buck, Gahanna, OH (US); Joseph Schaller, Reynoldsburg, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 193 days.

(21) Appl. No.: 14/654,092

(22) PCT Filed: Dec. 20, 2013

(86) PCT No.: PCT/US2013/077152
§ 371 (c)(1),
(2) Date: Jun. 19, 2015

(87) PCT Pub. No.: WO2014/100696
PCT Pub. Date: Jun. 26, 2014

(65) Prior Publication Data
US 2016/0256479 A1    Sep. 8, 2016

Related U.S. Application Data

(60) Provisional application No. 61/739,923, filed on Dec. 20, 2012.

(51) Int. Cl.
| | | |
|---|---|---|
| *A61K 31/7028* | (2006.01) |
| *A61K 31/702* | (2006.01) |
| *A61K 45/06* | (2006.01) |
| *A61K 9/00* | (2006.01) |
| *A61K 31/015* | (2006.01) |
| *A61K 31/202* | (2006.01) |
| *A23L 5/00* | (2016.01) |

(Continued)

(52) U.S. Cl.
CPC ............ *A61K 31/7028* (2013.01); *A23L 2/52* (2013.01); *A23L 5/00* (2016.08); *A23L 29/30* (2016.08); *A23L 33/10* (2016.08); *A23L 33/105* (2016.08); *A23L 33/115* (2016.08); *A23L 33/12* (2016.08); *A23L 33/125* (2016.08); *A23L 33/15* (2016.08); *A23L 33/21* (2016.08); *A23L 33/22* (2016.08); *A23L 33/40* (2016.08); *A61K 9/0095* (2013.01); *A61K 31/015* (2013.01); *A61K 31/202* (2013.01); *A61K 31/702* (2013.01); *A61K 45/06* (2013.01); *A23L 7/00* (2016.08); *A23L 9/00* (2016.08); *A23L 21/00* (2016.08); *A23V 2002/00* (2013.01); *A23V 2200/324* (2013.01);

*A23V 2250/032* (2013.01); *A23V 2250/0612* (2013.01); *A23V 2250/154* (2013.01); *A23V 2250/1578* (2013.01); *A23V 2250/1586* (2013.01); *A23V 2250/1588* (2013.01); *A23V 2250/1592* (2013.01); *A23V 2250/1598* (2013.01); *A23V 2250/16* (2013.01); *A23V 2250/161* (2013.01); *A23V 2250/1608* (2013.01); *A23V 2250/1612* (2013.01); *A23V 2250/1614* (2013.01); *A23V 2250/1626* (2013.01); *A23V 2250/1642* (2013.01); *A23V 2250/1842* (2013.01); *A23V 2250/28* (2013.01); *A23V 2250/304* (2013.01); *A23V 2250/5036* (2013.01); *A23V 2250/5054* (2013.01); *A23V 2250/5108* (2013.01); *A23V 2250/5114* (2013.01); *A23V 2250/5424* (2013.01); *A23V 2250/5488* (2013.01); *A23V 2250/54246* (2013.01); *A23V 2250/54252* (2013.01); *A23V 2250/61* (2013.01); *A23V 2250/628* (2013.01); *A23V 2250/702* (2013.01); *A23V 2250/705* (2013.01); *A23V 2250/706* (2013.01); *A23V 2250/708* (2013.01); *A23V 2250/7044* (2013.01); *A23V 2250/7046* (2013.01); *A23V 2250/7056* (2013.01); *A23V 2250/7058* (2013.01); *A23V 2250/712* (2013.01); *A23V 2250/7106* (2013.01); *A23V 2250/72* (2013.01)

(58) Field of Classification Search
None
See application file for complete search history.

(56) References Cited

U.S. PATENT DOCUMENTS 6,083,934 A * 7/2000 Prieto .................... A23C 9/203
424/405
2009/0118229 A1    5/2009 Jouni et al.
(Continued)

FOREIGN PATENT DOCUMENTS

EP    2060257    5/2009
EP    2455387    5/2012
(Continued)

OTHER PUBLICATIONS

Nunn, Br J Clin Pharmacol 59:6, pp. 674-676, 2005.*
(Continued)

*Primary Examiner* — Layla D Berry
(74) *Attorney, Agent, or Firm* — Calfee, Halter & Griswold LLP

(57) ABSTRACT

Disclosed is a nutritional composition for use in modulating or reducing inflammation in an adult or elderly individual in need thereof. In some aspects, the nutritional composition comprises a neutral human milk oligosaccharide.

6 Claims, 1 Drawing Sheet

(51) Int. Cl.
  *A23L 33/125* (2016.01)
  *A23L 33/21* (2016.01)
  *A23L 2/52* (2006.01)
  *A23L 33/10* (2016.01)
  *A23L 29/30* (2016.01)
  *A23L 33/105* (2016.01)
  *A23L 33/15* (2016.01)
  *A23L 33/115* (2016.01)
  *A23L 33/12* (2016.01)
  *A23L 33/00* (2016.01)
  *A23L 33/22* (2016.01)
  *A23L 7/00* (2016.01)
  *A23L 21/00* (2016.01)
  *A23L 9/00* (2016.01)

(56) References Cited

U.S. PATENT DOCUMENTS

| | | | |
|---|---|---|---|
| 2012/0172307 A1 | 7/2012 | Davis et al. | |
| 2012/0172327 A1 | 7/2012 | Buck et al. | |
| 2012/0172330 A1* | 7/2012 | Buck | A61K 31/7016 514/61 |
| 2012/0172331 A1 | 7/2012 | Buck et al. | |

FOREIGN PATENT DOCUMENTS

| | | |
|---|---|---|
| WO | WO2011/005681 A * | 1/2011 |
| WO | WO2011005681 A2 * | 1/2011 |
| WO | 2012/092153 | 7/2012 |
| WO | 2012/092154 | 7/2012 |
| WO | 2012/092157 | 7/2012 |
| WO | 2012/092159 | 7/2012 |

OTHER PUBLICATIONS

Bode, Human milk oligosaccharides inhibit PNC formation, Journal of Leukocyte Biology, vol. 76, Oct. 2004.*
Significant p-values in small samples, internet article posted Jan. 25, 2012, allenfleishmanbiostatistics.com/Articles/2012/13-p-values-in-small-samples/.*
Office Action in CN Application No. 201380067062.8 dated Feb. 7, 2017.
Bode, "Human milk oligosaccharides: Every baby needs a sugar mama," Glycobiology vol. 22 No. 9 pp. 1147-1162, Apr. 18, 2012.
International Search Report and Written Opinion for PCT/US2013/077152 dated Feb. 20, 2014.
Office Action in CN Application No. 201380067062.8 dated Jul. 6, 2017.
Search Report from European Application No. 13818953.5 dated Sep. 15, 2017.
Notice of Reexamination in CN Application No. 201380067062.8 dated Mar. 4, 2019.
Search Report from European Application No. 18211343.1 dated Mar. 15, 2019.
Office Action from Taiwan Application No. 102147669 dated Nov. 20, 2018.
Office Action in CN Application No. 201380067062.8 dated Aug. 8, 2019.

* cited by examiner

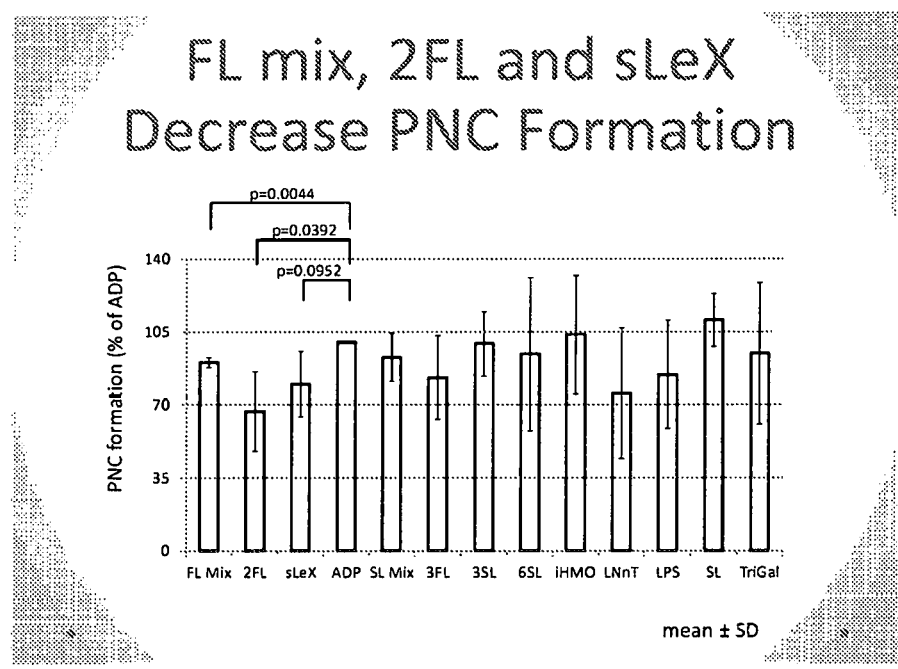

NUTRITIONAL FORMULATIONS USING HUMAN MILK OLIGOSACCHARIDES FOR MODULATING INFLAMMATION

CROSS-REFERENCE TO RELATED APPLICATIONS

This application is the U.S. national phase entry of PCT/US2013/077152, with an international filing date of Dec. 20, 2013, which claims priority to and any benefit of U.S. Provisional Application No. 61/739,923 filed Dec. 20, 2012, the entire contents of which are incorporated by reference in their entirety.

FIELD OF THE DISCLOSURE

The present disclosure relates to a nutritional composition for use in modulating or reducing inflammation in an adult or elderly individual in need thereof. More particularly, in some aspects, the nutritional composition reduces inflammation and the incidence of inflammatory diseases by reducing platelet neutrophil complex (PNC) formation. In some aspects, the nutritional composition comprises a neutral human milk oligosaccharide.

BACKGROUND OF THE DISCLOSURE

An inflammatory response is an attempt by the body to restore and maintain homeostasis after invasion by an infectious agent, antigen challenge, or physical, chemical or traumatic damage. While the inflammatory response is generally considered a healthy response to injury, the immune system can present an undesirable physiological response if it is not appropriately regulated. Specifically, unregulated oxidation and associated inflammation are major causes of tissue damage and clinically significant disease in adults and the elderly, oncology patients, for instance.

Breast milk containing HMOs has been associated with enhanced development and balanced growth and maturation of the infant's respiratory, gastrointestinal and immune systems, thereby providing protection to the infant from infection and inflammatory diseases. Breast milk appears to contain endogenous antioxidants, such as superoxide dismutase, glutathione peroxidase and catalase, or other non-enzymatic antioxidants such as glutathione, lactoferrin and polyphenols, in addition to exogenous antioxidants, such as vitamins A, C, E and selenium. Further, breast milk includes HMOs that not only act as pathogen receptor analogues, but activate immune factors. The function of these breast milk components, functioning as antioxidants and as immune modulators, includes not only the protection of breast milk lipids by peroxidation, but may also assist in the regulation of inflammatory responses to infection or other injury.

No vaccines are currently available for the minimization of inflammatory diseases. Therefore, development of safe and efficacious preventative or therapeutic methods would be beneficial, especially for adults and the elderly. It would therefore be desirable to provide nutritional compositions, and adult nutritional composition formulas in particular, that can produce nutritional benefits including improved immune system support and response. It would additionally be beneficial if the nutritional compositions could modulate inflammation and enhance immunity against microbial infections, including bacterial and viral infections, and other inflammatory diseases.

SUMMARY OF THE DISCLOSURE

In one aspect, the present disclosure is directed to a nutritional composition for use in modulating or reducing inflammation in an adult or elderly individual in need thereof, the nutritional composition comprising a neutral human milk oligosaccharide in a concentration of from about 0.001 mg/mL to about 25 mg/mL. Neutral HMOs that are particularly suitable for the nutritional compositions include at least one of 2'-fucosyllactose (2'FL) and lacto-N-neotetraose (LNnT), and in particular, the combination of 2'FL and 3-fucosyllactose (3FL), and the combination of 3FL and LNnT.

BRIEF DESCRIPTION OF THE DRAWINGS

FIG. 1. 2'FL and the FL Mix are shown to significantly decrease PNC Formation. Incubation at 15 minutes was optimal.

DETAILED DESCRIPTION OF THE DISCLOSURE

The terms "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step, to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "human milk oligosaccharide" or "HMO" as used herein, unless otherwise specified, refers generally to a number of complex carbohydrates found in human breast milk that can be in acidic or neutral form, and to precursors thereof. Exemplary non-limiting neutral human milk oligosaccharides include 3-fucosyllactose, 2'-fucosyllactose, and lacto-N-neo-tetraose (LNnT). Exemplary human milk oligosaccharide precursors include lactose, fucose, or any combination thereof. "Neutral human milk oligosaccharides" refer generally to neutral oligosaccharides which are comprised of monosaccharides that are not charged at physiological pH, i.e., do not contain a residue or moiety of the sialic acids (N-Acetyl-Neuraminic or N-glycolyl-Neuraminic Acid) and also lack glucosamine (i.e. non-acetylated glucosamine). The range of concentration for neutral HMOs may be from about 0.001 mg/mL to about 25 mg/mL. Accordingly, examples of weight ranges for 2'-fucosyllactose may be from about 0.001 mg/mL to about 25 mg/mL; and LNnT may be in the range from about 0.001 mg/mL to about 25 mg/mL.

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The terms "nutritional formulation" or "nutritional composition" as used herein, are used interchangeably and, unless otherwise specified, refer to synthetic formulas including nutritional liquids, nutritional powders, nutritional solids, nutritional semi-solids, nutritional semi-liquids, nutritional supplements, and any other nutritional food product as known in the art. The nutritional powders may be reconstituted to form a nutritional liquid, all of which comprise one or more of fat, protein and carbohydrate and are suitable for oral consumption by a human. The terms "nutritional formulation" or "nutritional composition" do not include human breast milk.

The term "nutritional liquid" as used herein, unless otherwise specified, refers to nutritional products in ready-to-drink liquid form, concentrated form, and nutritional liquids made by reconstituting the nutritional powders described herein prior to use.

The term "nutritional powder" as used herein, unless otherwise specified, refers to nutritional products in flowable or scoopable form that can be reconstituted with water or another aqueous liquid prior to consumption and includes both spraydried and drymixed/dryblended powders.

The term "nutritional semi-solid," as used herein, unless otherwise specified, refers to nutritional products that are intermediate in properties, such as rigidity, between solids and liquids. Some semi-solids examples include puddings, gelatins, and doughs.

The term "nutritional semi-liquid," as used herein, unless otherwise specified, refers to nutritional products that are intermediate in properties, such as flow properties, between liquids and solids. Some semi-liquids examples include thick shakes and liquid gels.

The term "adult" as used herein refers to adults and children about 12 years of age and older.

The term "elderly individual" as used herein, as used herein, refers to an individual of at least 45 years of age, including at least 50 years of age, at least 55 years of age, at least 60 years of age, at least 65 years of age, at least 70 years of age, at least 75 years of age, and including at least 80 years or age or greater. The term "elderly" also includes the groups of from about 45 years of age to about 95 years of age, and the group of from about 55 years of age to about 80 years of age.

The terms "absence of a virus" or "absent a virus" as used herein with respect to inducing production of monocyte-derived cytokines, unless otherwise specified, refer to an individual without the virus or having the virus in an amount less than the amount required to illicit an immune response; that is, an amount that is less than required for the body's natural immune response to increase the production of cytokines and other immune factors.

The terms "inflammatory disease" or "inflammatory condition" as used herein, unless otherwise specified, refer to any disease, disorder, or condition characterized by inflammation. The term "infection-mediated inflammatory disease" as used herein, unless otherwise specified, refers to an inflammatory disease associated or induced by microbial infection, including viral and bacterial infection.

The terms "susceptible" and "at risk" as used herein, unless otherwise specified, mean having little resistance to a certain condition or disease, including being genetically predisposed, having a family history of, and/or having symptoms of the condition or disease.

The terms "modulating" or "modulation" or "modulate" as used herein, unless otherwise specified, refer to the targeted movement of a selected characteristic.

The term "ameliorate" as used herein, unless otherwise specified, means to eliminate, delay, or reduce the prevalence or severity of symptoms associated with a condition.

The term "an effective amount" is intended to qualify the amount of HMO which will achieve the goal of decreasing the risk that the patient will suffer an adverse health event, while avoiding adverse side effects such as those typically associated with alternative therapies. The effective amount may be administered in one or more doses The terms "treating" and "treatment" as used herein, unless otherwise specified, includes delaying the onset of a condition, reducing the severity of symptoms of a condition, or eliminating some or all of the symptoms of a condition.

The terms "growth of a virus" or "growth of bacteria" as used herein, unless otherwise specified, refer to the production, proliferation, or replication of a virus or bacteria.

The term "food products" as used herein refer to delivery vehicles that contain one or more of fats, amino nitrogen and carbohydrates and provides some or all of the nutritional support for a patient in the recommended daily amounts. Frequently a food product will contain vitamins, minerals, trace minerals and the like to provide balanced nutrition to meal replacements, medical foods, supplements. The food products may be in any typical form such as beverages, powders, bars, juices, carbonated beverages, bottled water.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

A decrease in PNC (platelet neutrophil complex) formation is suggestive of a decrease in inflammation. The current literature shows that a pooled mixture of acidic oligosaccharides decreases PNC formation. The current literature also shows that a pooled mixture of neutral oligosaccharides does not decrease PNC formation, or decrease CD11b expression. In contrast to prior results, experimental results provided herein show that the individual neutral human milk oligosaccharides 2'-fucosyllactose (2'FL) and lacto-N-neo-tetraose (LNnT), alone or in combination with 3-fucosyllactose (3FL), decreased PNC formation. Further, 3FL alone did not decrease PNC formation. In further contrast to the prior results and in contrast to the results for neutral oligosaccharides, the results provided herein shown that the acidic HMOs 3'-sialyllactose (3'SL) and 6'-sialyllactose (6'SL) did not decrease PNC formation; and neither did the acidic HMO precursor, sialic acid (SL).

It has been discovered that specific neutral HMOs, such as 2'-fucosyllactose and lacto-N-neotetraose, and a combination of 2'- and 3-fucosyllactose, are highly effective in dampening inflammation generally in adults, and specifically in dampening virus-induced inflammation, including respiratory syncytial virus, human parainfluenza, and influenza A, by reducing the production of some key cytokines from human immune cells without increasing viral load, which may lead to faster recovery from infections.

Populations which have an increase in PNC formation (platelet-neutrophil complex) and thus an increase in inflammation, and which could benefit from a decrease in inflammation include diabetics, especially women, ischemic patients, active sickle cell disease patients, patients with vascular inflammation, and patients suffering from a microbial infection (respiratory or gastrointestinal infection, sepsis, periodontitis). Further benefiting are those adults and elderly individuals at risk of chronic inflammation. This may include athletes, elderly, those with asthma or allergies, and those with inflammatory bowel disease (IBD) could also benefit from the decrease in PNC formation and resulting inflammation.

Surprisingly, it was determined that these neutral HMOs demonstrate the desirable dampening effects even at very low concentrations, including concentrations lower than those found in human breast milk.

Moreover, it has been discovered that specific neutral HMOs act in a synergistic manner against respiratory viruses, including RSV, when combined with a long chain polyunsaturated fatty acid and/or a carotenoid. These synergistic actions dampen virus-induced inflammatory cytokines, and specifically interferon-inducible protein 10 (IP-10). Additional components including antioxidants, such as vitamin A and vitamin E, or nucleotides, may also be added to the HMO(s) and long chain polyunsaturated fatty acid and/or carotenoid combinations.

It has also been found that the neutral HMO 2'-fucosyllactose and a mixture of 2'-fucosyllactose and 3-fucosyllactose decrease platelet neutrophil complex (PNC) formation. Also, LNnT decreased PNC formation in 2 out of 3 individuals.

The nutritional compositions and methods described herein utilize neutral HMOs alone or in combination with one or more of long chain polyunsaturated fatty acids, antioxidants, including carotenoids, and nucleotides, for controlling and reducing a number of diseases and conditions related to inflammation. In some aspects, the nutritional compositions described herein include synthetic formulas that include one neutral HMO, a combination of neutral HMOs, or one or more neutral HMOs in combination with one or more of long chain polyunsaturated fatty acids, antioxidants, including carotenoids, and nucleotides. These and other features of the nutritional compositions, methods, and uses thereof, as well as some of the many optional variations and additions, are described in detail hereafter.

The neutral HMOs can be formulated in suitable compositions and then, in accordance with the methods of the invention, administered to a patient in a form adapted to the chosen route of administration. The formulations include, but are not limited to, those suitable for oral or parental (including subcutaneous, intramuscular, intraperitoneal, intratumoral, and intravenous) administration. Oral administration, as defined herein, includes any form of administration in which the neutral HMO passes through the esophagus of the patient. For example, oral administration includes nasogastric intubation, in which a tube is run from through the nose to the stomach of the patient to administer food or drugs.

Oral formulations include any solid, liquid, or powder formulation suitable for use herein, provided that such a formulation allows for the safe and effective oral delivery of the neutral HMO and optional nutritive components. In preferred embodiments, the oral formulation is a liquid nutritional composition. Formulations of the present invention suitable for oral administration may be presented as discrete units such as tablets, troches, capsules, lozenges, wafers, or cachets, each containing a predetermined amount of the neutral HMO as a powder or granules or as a solution or suspension in an aqueous liquor or non-aqueous liquid such as a syrup, an elixir, an emulsion, or a draught.

The nutritional compositions and methods may comprise, consist of, or consist essentially of the essential elements of the compositions and methods as described herein, as well as any additional or optional element described herein or otherwise useful in nutritional product applications.

Human Milk Oligosaccharides

The nutritional compositions of the present disclosure include at least one neutral HMO, and in many embodiments, a combination of two or more neutral HMOs. Oligosaccharides are one of the main components of human breast milk, which contains, on average, 10 grams per liter of neutral oligosaccharides and 1 gram per liter of acidic oligosaccharides. The composition of human milk oligosaccharides is very complex and more than 200 different oligosaccharide-like structures are known.

The neutral HMO or HMOs may be isolated or enriched from milk(s) secreted by mammals including, but not limited to: human, bovine, ovine, porcine, or caprine species. The neutral HMOs may also be produced via microbial fermentation, enzymatic processes, chemical synthesis, or combinations thereof.

Suitable neutral HMOs for use in the nutritional compositions include fucosyl oligosaccharides (i.e., lacto-n-fucopentaose I; lacto-n-fucopentaose II; lacto-n-fucopentaose III; lacto-n-difucohexaose I; and lactodifucotetraose); non-fucosylated, non-sialylated oligosaccharides (i.e., lacto-n-tetraose and lacto-n-neotetraose). Neutral HMOs that are particularly suitable for the nutritional compositions include at least one of the following HMOs or HMO precursors: 2'-fucosyllactose (2'FL); 3-fucosyllactose (3FL); lacto-N-tetraose (LNT) and lacto-N-neotetraose (LNnT), and in particular, combinations of 2'FL and 3FL; and combinations of 3FL and LNnT. In addition to the neutral HMOs described above, the nutritional compositions may include other neutral HMOs, acidic HMOs, or acidic or neutral HMO precursors that are known in the art.

The neutral HMOs are present in the nutritional compositions in total amounts of neutral HMO in the composition (mg of neutral HMO per mL of composition) of at least about 0.001 mg/mL, including at least about 0.01 mg/mL, and also including from about 0.001 mg/mL to about 25 mg/mL, including from about 0.01 mg/mL to about 20 mg/mL, including from about 0.01 mg/mL to about 10 mg/mL, including from about 0.01 mg/mL to about 5 mg/mL, including from about 0.01 mg/mL to about 1 mg/mL, and also including from about 0.001 mg/mL to about 1 mg/mL, including from about 0.001 mg/mL to about 0.23 mg/mL, including from about 0.01 mg/mL to about 0.23 mg/mL of total neutral HMO in the nutritional composition. Typically, the amount of neutral HMO in the nutritional composition will depend on the specific neutral HMO or neutral HMOs present and the amounts of other components in the nutritional compositions.

In one specific embodiment, the nutritional composition includes a neutral human milk oligosaccharide in an amount of from about 0.001 mg/mL to about 25 mg/mL, including from about 0.001 mg/mL to less than about 2 mg/mL, and also including from about 0.01 mg/mL to about 25 mg/mL, including from about 0.01 mg/mL to less than about 2 mg/mL.

In another embodiment, the nutritional composition includes one or more neutral human milk oligosaccharides selected from 2'-fucosyllactose and lacto-N-neotetraose.

In one specific embodiment, the nutritional composition includes LNnT, alone or in combination with other HMOs, in a concentration of from about 0.001 mg/mL to about 25 mg/mL, including from about 0.001 mg/mL to less than 0.2 mg/mL, also including from about 0.01 mg/mL to about 25 mg/mL, including from about 0.01 mg/mL to less than about 0.2 mg/mL, and also including from greater than about 0.32 mg/mL to about 20 mg/mL, and also including from about 0.1 mg/mL to about 5 mg/mL.

In another specific embodiment, the nutritional composition includes 2'FL, alone or in combination with other HMOs, in an amount of from about 0.001 mg/mL to about 25 mg/mL, including from about 0.001 mg/mL to about 15 mg/mL, including from about 0.001 mg/mL to less than about 2 mg/mL, including from about 0.001 mg/mL to less than about 1 mg/mL, also including from about 0.01 mg/mL to about 25 mg/mL, including from about 0.01 mg/mL to about 20 mg/mL, including from about 0.01 mg/mL to less than about 2 mg/mL, including from about 0.01 mg/mL to less than about 1 mg/mL, and also including from greater than 1.7 mg/mL to about 20 mg/mL, including greater than about 2.5 mg/mL to about 20 mg/mL, and also including from about 0.050 mg/mL to about 10 mg/mL, including from about 0.1 mg/mL to about 10 mg/mL.

In one specific embodiment, the nutritional composition includes 2'FL or LNnT in combination with 3FL in a total amount of HMO of from about 0.001 mg/mL to about 25 mg/mL, including from about 0.01 mg/mL to about 25 mg/mL of total HMO, where 3FL is present in the nutritional composition in a concentration of from about 0.001 mg/ML to about 10 mg/mL.

Long Chain Polyunsaturated Fatty Acids (LCPUFAs)

In addition to the HMOs described above, the nutritional products of the present disclosure may include LCPUFAs. LCPUFAs are included in the nutritional compositions to provide nutritional support, as well as to reduce oxidative stress and enhance growth and functional development of the intestinal epithelium and associated immune cell populations. In some embodiments, the nutritional composition includes a combination of one or more neutral HMOs and one or more LCPUFAs such that the composition provides a synergistic benefit to the end user, such as a synergistic benefit in modulating anti-viral immune responses and dampening inflammation.

Exemplary LCPUFAs for use in the nutritional compositions include, for example, ω-3 LCPUFAs and ω-6 LCPUFAs. Specific LCPUFAs include docosahexaenoic acid (DHA), eicosapentaenoic acid (EPA), docosapentaenoic acid (DPA), arachidonic acid (ARA), linoleic acid, linolenic acid (alpha linolenic acid) and gamma-linolenic acid derived from oil sources such as plant oils, marine plankton, fungal oils, krill oil and fish oils. In one particular embodiment, the LCPUFAs are derived from fish oils such as menhaden, salmon, anchovy, cod, halibut, tuna, or herring oil. Particularly preferred LCPUFAs for use in the nutritional compositions with the neutral HMOs include DHA, ARA, EPA, DPA, and combinations thereof.

In order to reduce potential side effects of high dosages of LCPUFAs in the nutritional compositions, the content of LCPUFAs preferably does not exceed 5% by weight of the total fat content, including below 2% by weight of the total fat content, and including below 1% by weight of the total fat content in the nutritional composition.

The LCPUFA may be provided as free fatty acids, in triglyceride form, in diglyceride form, in monoglyceride form, in phospholipid form, in esterified form or as a mixture of one or more of the above, preferably in triglyceride form.

The nutritional compositions as described herein will typically comprise total concentrations of LCPUFA of from about 0.01 mM to about 10 mM and including from about 0.01 mM to about 1 mM. Alternatively, the nutritional compositions comprise total concentrations of LCPUFA of from about 0.001 g/L to about 1 g/L.

In one embodiment, the nutritional compositions include total long chain ω-6 fatty acids in a concentration of from about 100 to about 425 mg/L or from about 12 to about 53 mg per 100 kcals and/or further include total long chain ω-3 fatty acids in a concentration of from about 40 to about 185 mg/L or from about 5 to about 23 mg per 100 kcals. In one specific embodiment, the ratio of long chain ω-6 fatty acids to long chain ω-3 fatty acids in the nutritional compositions ranges from about 2:1 to about 3:1, preferably about 2.5:1.

In one specific embodiment, the nutritional compositions include DHA in a concentration of from about 0.025 mg/mL to about 0.130 mg/mL or from about 3 to about 16 mg per 100 kcals. In another embodiment, the nutritional compositions include ARA in a concentration of from about 0.080 mg/mL to about 0.250 mg/mL or from about 10 to about 31 mg per 100 kcals. In yet another embodiment, the nutritional compositions include combinations of DHA and ARA such that the ratio of DHA to ARA ranges from about 1:4 to about 1:2.

Antioxidants

Additionally, the nutritional compositions may comprise one or more antioxidants in combination with the neutral HMOs (and optionally LCPUFAs and/or nucleotides also) to provide nutritional support, as well as to reduce oxidative stress. In some embodiments, the nutritional composition includes a combination of neutral HMOs and antioxidants such that the composition provides a synergistic benefit to the end user, such as a synergistic benefit in modulating anti-viral immune responses and dampening inflammation. In some embodiments, carotenoids are used as the antioxidants (and specifically lutein, beta-carotene, zeaxanthin and/or lycopene) to provide the synergistic effect.

Any antioxidants suitable for oral administration may be included for use in the nutritional compositions of the present disclosure, including, for example, vitamin A, vitamin E, vitamin C, retinol, tocopherol, and carotenoids, including lutein, beta-carotene, zeaxanthin, and lycopene, and combinations thereof, for example.

As noted, the antioxidants used in the nutritional compositions may be used with the neutral HMOs alone, or in combination with LCPUFAs and/or nucleotides. In one specific embodiment, the antioxidants for use in the nutritional compositions include carotenoids, and particularly, combinations of the carotenoids lutein, lycopene, zeaxanthin and/or beta-carotene. Nutritional compositions containing these combinations, as selected and defined herein, can be used to modulate inflammation and/or levels of C-reactive protein.

It is generally preferable that the nutritional compositions comprise at least one carotenoid selected from lutein, lycopene, zeaxanthin, and beta-carotene to provide a total amount of carotenoid of from about 0.001 μg/mL to about 10 μg/mL. More particularly, the nutritional compositions comprise lutein in an amount of from about 0.001 μg/mL to about 10 μg/mL, including from about 0.001 μg/mL to about 5 μg/mL, including from about 0.001 μg/mL to about 0.0190 μg/mL, including from about 0.001 μg/mL to about 0.0140 μg/mL, and also including from about 0.044 μg/mL to about 5 μg/mL of lutein. It is also generally preferable that the nutritional compositions comprise from about 0.001 μg/mL to about 10 μg/mL, including from about 0.001 μg/mL to about 5 μg/mL, from about 0.001 μg/mL to about 0.0130 μg/mL, including from about 0.001 μg/mL to about 0.0075 μg/mL, and also including from about 0.0185 μg/mL to about 5 μg/mL of lycopene. It is also generally preferable that the nutritional compositions comprise from about 1 μg/mL to about 10 μg/mL, including from about 1 μg/mL to about 5 μg/mL, including from about 0.001 μg/mL to about 0.025 μg/mL, including from about 0.001 μg/mL to about 0.011 μg/mL, and also including from about 0.034 μg/mL to about 5 μg/mL of beta-carotene. It should be understood that any combination of these amounts of beta-carotene, lutein, zeaxanthin, and lycopene can be included in the nutritional compositions of the present disclosure. Other carotenoids may optionally be included in the nutritional compositions as described herein. Any one or all of the carotenoids included in the nutritional compositions described herein may be from a natural source, or artificially synthesized. In one particular embodiment, the nutritional composition comprises a combination of the neutral HMO, 2'FL, and lycopene.

The carotenoids can be obtained from any known or otherwise suitable material source for use in nutritional compositions, and each can be provided individually, or all together, or in any combination and from any number of sources, including sources such as multivitamin premixes containing other vitamins or minerals in combination with one or more of the carotenoids as described herein. Non-limiting examples of some suitable sources of lutein, lycopene, beta-carotene, or combinations thereof include Lyco-Vit® lycopene (available from BASF, Mount Olive, N.J.), Lyc-O-Mato® tomato extract in oil, powder, or bead form (available from LycoRed Corp., Orange, N.J.), beta-carotene, lutein, or lycopene (available from DSM Nutritional Products, Parsippany, N.J.), FloraGLO® lutein (available from Kemin Health, Des Moines, Iowa), Xangold® Natural Lutein Esters (available from Cognis, Cincinnati, Ohio), and Lucarotin® beta-carotene (available from BASF, Mount Olive, N.J.).

Nucleotides

In addition to the neutral HMOs, the nutritional compositions of the present disclosure may additionally comprise nucleotides and/or nucleotide precursors selected from the group consisting of nucleosides, purine bases, pyrimidine bases, ribose and deoxyribose. The nucleotide may be in monophosphate, diphosphate, or triphosphate form. The nucleotide may be a ribonucleotide or a deoxyribonucleotide. The nucleotides may be monomeric, dimeric, or polymeric (including RNA and DNA). The nucleotide may be present in the nutritional composition as a free acid or in the form of a salt, preferably a monosodium salt. In some embodiments, the nutritional composition includes a combination of neutral HMOs and nucleotides such that the composition provides a synergistic benefit to the end user, such as a synergistic benefit in modulating anti-viral immune responses and dampening inflammation and/or improving intestinal barrier integrity.

Incorporation of nucleotides in the nutritional compositions of the present disclosure improves intestinal barrier integrity, maturation, or both.

Suitable nucleotides and/or nucleosides for use in the nutritional compositions include one or more of cytidine 5'-monophosphate, uridine 5'-monophosphate, adenosine 5'-monophosphate, guanosine 5'-1-monophosphate, and/or inosine 5'-monophosphate, more preferably cytidine 5'-monophosphate, uridine 5'-monophosphate, adenosine 5'-monophosphate, guanosine 5'-monophosphate, and inosine 5'-monophosphate.

The nutritional compositions including the neutral HMO or HMOs may be formulated to include at least one of protein, fat, and carbohydrate. In many embodiments, the nutritional compositions will include the neutral HMO or HMOs with protein, carbohydrate and fat. Although total concentrations or amounts of the fat, protein, and carbohydrates may vary depending upon the product type (i.e., nutritional formula), product form (i.e., nutritional solid, powder, ready-to-feed liquid, or concentrated liquid) and targeted dietary needs of the intended user, such concentrations or amounts most typically fall within one of the following embodied ranges, inclusive of any other essential fat, protein, and/or carbohydrate ingredients as described herein.

Fat

The nutritional compositions of the present disclosure may, in addition to the LCPUFAs, comprise an additional source or sources of fat. Suitable additional sources of fat for use herein include any fat or fat source that is suitable for use in an oral nutritional product and is compatible with the essential elements and features of such products. Most typically the fat may be an emulsified fat, concentrations of which may range from about 1% to about 30%, including from about 2% to about 15%, and also including from about 4% to about 10%, by weight. In one specific embodiment, the additional fat is derived from short chain fatty acids.

Additional non-limiting examples of suitable fats or sources thereof for use in the nutritional products described herein include coconut oil, fractionated coconut oil, soybean oil, corn oil, olive oil, safflower oil, high oleic safflower oil, oleic acids (EMERSOL 6313 OLEIC ACID, Cognis Oleochemicals, Malaysia), MCT oil (medium chain triglycerides), sunflower oil, high oleic sunflower oil, palm and palm kernel oils, palm olein, canola oil, marine oils, fish oils, fungal oils, algae oils, cottonseed oils, and combinations thereof. Lipid sources of arachidonic acid and docosahexaenoic acid include, but are not limited to, marine oil, egg yolk oil, and fungal or algal oil.

Numerous commercial sources for these fats are readily available and known to one practicing the art. For example, soy and canola oils are available from Archer Daniels Midland of Decatur, Ill. Corn, coconut, palm and palm kernel oils are available from Premier Edible Oils Corporation of Portland, Org. Fractionated coconut oil is available from Henkel Corporation of LaGrange, Ill. High oleic safflower and high oleic sunflower oils are available from SVO Specialty Products of Eastlake, Ohio. Marine oil is available from Mochida International of Tokyo, Japan. Olive oil is available from Anglia Oils of North Humberside, United Kingdom. Sunflower and cottonseed oils are available from Cargil of Minneapolis, Minn. Safflower oil is available from California Oils Corporation of Richmond, Calif.

In addition to these food grade oils, structured lipids may be incorporated into the food product if desired. Structured lipids are known in the art. A concise description of structured lipids can be found in INFORM, Vol. 8, No. 10, page 1004; entitled Structured lipids allow fat tailoring (October 1997). Also see U.S. Pat. No. 4,871,768. Structured lipids are predominantly triacylglycerols containing mixtures of medium and long chain fatty acids on the same glycerol nucleus. Structured lipids and their use in enteral formula are also described in U.S. Pat. Nos. 6,194,379 and 6,160,007.

Optionally, ω-3 fatty acids may comprise up to approximately 30% of the oil blend, preferably the ω-3 fatty acids largely consist of the longer chain forms, cicosapentaenoic acid (EPA) and docosahexaenoic acid (DHA). Dietary oils used in the preparation of the nutritional composition generally contain ω-3 fatty acids in the triglyceride form and include, but are not limited to canola, medium chain triglycerides, fish, soybean, soy lecithin, corn, safflower, sunflower, high-oleic sunflower, high-oleic safflower, olive, borage, black currant, evening primrose and flaxseed oil. Optionally, the weight ratio of ω-6 fatty acids to ω-3 fatty acids in the lipid blend according to the invention is about 0.1 to 3.0. The daily delivery of ω-3 fatty acids should be at least 450 mg and may vary depending on body weight, sex, age and medical condition of the individual. As mentioned, higher levels are desired for adult human consumption: for example, from about 0.5 to 50 gm daily, more preferably from about 2.5 to 5 gm daily Protein The nutritional products may further comprise any protein or sources thereof that are suitable for use in oral nutritional products and are compatible with the essential elements and features of such products. Total protein concentrations in the nutritional liquids may range from about 0.5% to about 30%, including from about 1% to about 15%, including from about 2% to about 10%, and also including from about 3% to about 8%, including from about 3% to about 7%, and including from about 3% to about 6.72% by weight. In one particular embodiment, when the nutritional product is an emulsion, the emulsion includes protein in a total concentration of about 6.77% by weight. When the nutritional product is a substantially clear liquid, the clear liquid includes protein in a total concentration of from about 3.00% to about 4.47% by weight.

Non-limiting examples of suitable proteins or sources thereof for use in the nutritional products include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy) or combinations thereof. Non-Limiting examples of such proteins include milk protein isolates, milk protein concentrates as described herein, casein protein isolates, extensively hydrolyzed casein, whey protein, sodium or calcium caseinates, whole cow milk, partially or completely defatted milk, soy protein isolates, soy protein concentrates, and so forth. In one specific embodiment, the nutritional compositions include a protein source derived from milk proteins of human and/or bovine origin.

The protein in the nutritional products may include intact proteins as that term is defined herein to improve product stability and minimize the development of bitter flavors and after taste in the formulation during shelf life.

Carbohydrate

The nutritional products may further comprise any carbohydrates that are suitable for use in an oral nutritional product and are compatible with the essential elements and features of such products. Carbohydrate concentrations in the nutritional liquids, for example, may range from about 5% to about 40%, including from about 7% to about 30%, including from about 10% to about 25%, by weight.

Non-limiting examples of suitable carbohydrates or sources thereof for use in the nutritional products described herein may include maltodextrin, hydrolyzed or modified starch or cornstarch, glucose polymers, corn syrup, corn syrup solids, rice-derived carbohydrates, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia) and combinations thereof. A particularly desirable carbohydrate is a low dextrose equivalent (DE) maltodextrin.

Other Optional Ingredients

The nutritional compositions of the present disclosure may further comprise other optional components that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, emulsifying agents, buffers, nucleotides, fructooligosaccharides, fiber, galactooligosaccharides, polydextrose, and other probiotics, probiotics, pharmaceutical actives, anti-inflammatory agents, additional nutrients as described herein, colorants, flavors, thickening agents and stabilizers, emulsifying agents, lubricants, and so forth.

The nutritional compositions may further comprise a sweetening agent, preferably including at least one sugar alcohol such as maltitol, erythritol, sorbitol, xylitol, mannitol, isolmalt, and lactitol, and also preferably including at least one artificial or high potency sweetener such as acesulfame K, aspartame, sucralose, saccharin, stevia, and tagatose. These sweetening agents, especially as a combination of a sugar alcohol and an artificial sweetener, are especially useful in formulating liquid beverage embodiments of the present disclosure having a desirable favor profile. These sweetener combinations are especially effective in masking undesirable flavors sometimes associated with the addition of vegetable proteins to a liquid beverage. Optional sugar alcohol concentrations in the nutritional product may range from at least 0.01%, including from about 0.1% to about 10%, and also including from about 1% to about 6%, by weight of the nutritional product. Optional artificial sweetener concentrations may range from about 0.01%, including from about 0.05% to about 5%, also including from about 0.1% to about 1.0%, by weight of the nutritional product.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in the nutritional composition varies depending upon the product form, the other selected ingredients, the desired flow properties, and so forth, but most typically range from about 0.1% to about 4%, including from about 0.5% to about 2%, by weight of the nutritional composition.

A stabilizer may also be included in the nutritional compositions. Any stabilizer that is known or otherwise suitable for use in a nutritional composition is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

The nutritional compositions may further comprise any of a variety of other vitamins or related nutrients, non-limiting examples of which include vitamin A, vitamin D, vitamin E, vitamin K, thiamine, riboflavin, pyridoxine, vitamin $B_{12}$, carotenoids (e.g., beta-carotene, zeaxanthin, lutein, lycopene), niacin, folic acid, pantothenic acid, biotin, vitamin C, choline, inositol, salts and derivatives thereof, and combinations thereof. The food products preferably include, but are not limited to, the following vitamins and minerals: calcium, phosphorus, sodium, chloride, magnesium, manganese, iron, copper, zinc, selenium, iodine, chromium, molybdenum, conditionally essential nutrients m-inositol, carnitine and taurine, and Vitamins A, C, D, E, K and the B complex, and mixtures thereof.

The conditionally essential nutrient carnitine is a naturally occurring amino acid formed from methionine and lysine. Its major metabolic role is associated with the transport of long-chain fatty acids across the mitochondrial membranes, thus stimulating the oxidation of these fuel substances for metabolic energy. Carnitine supplementation is an important metabolic tool in conditions such as diseases of the liver and kidney, and major chronic illnesses or extensive injuries complicated by malnutrition. Optionally, the meal replacements may be supplemented with carnitine at levels sufficient to supply up to 4 gm/day of carnitine.

The nutritional compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

The meal replacements also may contain fiber and stabilizers. Suitable sources of fiber/and or stabilizers include, but are not limited to, xanthan gum, guar gum, gum arabic, gum ghatti, gum karaya, gum tracaganth, agar, furcellaran, gellan gum, locust bean gum, pectin, low and high methoxy pectin, oat and barley glucans, carrageenans, psyllium, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, FOS (fructooligosaccharides), and mixtures thereof. Numerous commercial sources of soluble dietary fibers are available. For example, gum arabic, hydrolyzed carboxymethylcellulose, guar gum, pectin and the low and high methoxy pectins are available from TIC Gums, Inc. of Belcamp, Md. The oat and barley glucans are available from Mountain Lake Specialty Ingredients, Inc. of Omaha, Nebr. Psyllium is available from the Meer Corporation of North Bergen, N.J. while the carrageenan is available from FMC Corporation of Philadelphia, Pa.

The fiber incorporated may also be an insoluble dietary fiber representative examples of which include oat hull fiber, pea hull fiber, soy hull fiber, soy cotyledon fiber, sugar beet fiber, cellulose and corn bran. Numerous sources for the insoluble dietary fibers are also available. For example, the corn bran is available from Quaker Oats of Chicago, Ill.; oat hull fiber from Canadian Harvest of Cambridge, Minn.; pea hull fiber from Woodstone Foods of Winnipeg, Canada; soy hull fiber and oat hull fiber from The Fibrad Group of LaVale, Md.; soy cotyledon fiber from Protein Technologies International of St. Louis, Mo.; sugar beet fiber from Delta Fiber Foods of Minneapolis, Minn. and cellulose from the James River Corp. of Saddle Brook, N.J.

A more detailed discussion of examples of fibers and their incorporation into food products may be found in U.S. Pat. No. 5,085,883 issued to Garleb et al.

The quantity of fiber utilized in the formulas can vary. The particular type of fiber that is utilized is not critical. Any fiber suitable for human consumption and that is stable in the matrix of a food product may be utilized.

In addition to fiber, the nutritional compositions may also contain oligosaccharides such as fructooligosaccharides (FOS) or glucooligosaccharides (GOS). Oligosaccharides are rapidly and extensively fermented to short chain fatty acids by anaerobic microorganisms that inhabit the large bowel. These oligosaccharides are preferential energy sources for most *Bifidobacterium* species, but are not utilized by potentially pathogenic organisms such as *Clostridium perfingens, C. difficile*, or *Eschericia coli*.

The nutritional products may additionally comprise one or more thickeners (i.e., thickening agents). The addition of thickeners reduces the incidences of paresthesia by inducing the feeling of satiety, which prolongs gastric transit time as discussed above.

Exemplary thickeners include gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinogalactins, glucomannan, xanthan gum, alginate, pectin, low and high methoxy pectin, cereal beta-glucans (i.e., oat beta-glucan, barley beta-glucan), carrageenan and psyllium.

One particularly preferred thickener for use in the nutritional liquids is gellan gum. Gellan gum is a water-soluble polysaccharide produced by *Pseudomonas elodea*. As gellan gum is shear thinning, it can be used in the nutritional liquids without producing a viscous, unappealing textured product. Particularly preferred for use in the nutritional products of the present disclosure includes low acyl gellan gum. "Low acyl" gellan gum (also known as and commonly referred to as deacylated gellan gum) means that the gellan gum has been treated such that it forms firm, non-elastic, brittle gels, that are heat stable, as compared to "high acyl" which forms soft, very elastic, non-brittle gels. One suitable commercially available low acyl gellan gum is Kelcogel F (CP Kelco U.S. Inc., Atlanta Ga.).

The thickeners, and particularly gellan gum, are present in the nutritional liquids in concentrations ranging from about 0.03% to about 0.05%, including from about 0.035% to about 0.045%, and including about 0.04% by weight of the nutritional liquid.

The total amount or concentration of fat, carbohydrate, and protein, in the powdered nutritional compositions of the present disclosure can vary considerably depending upon the selected composition and dietary or medical needs of the intended user. Additional suitable examples of macronutrient concentrations are set forth below.

Product Forms

The nutritional compositions of the present disclosure may be formulated and administered in any known or otherwise suitable oral product form. Any solid, liquid, semi-solid, and semi-liquid, or powder product form, including combinations or variations thereof, are suitable for use herein, provided that such forms allow for safe and effective oral delivery to the individual of the essential ingredients as also defined herein.

The nutritional compositions may be in any product form comprising the ingredients described herein, and which is safe and effective for oral administration. The nutritional compositions may be formulated to include only the ingredients described herein, or may be modified with optional ingredients to form a number of different product forms.

The nutritional compositions of the present disclosure are desirably formulated as dietary product forms, which are defined herein as those embodiments comprising the ingredients of the present disclosure in a product form that then contains at least one of fat, protein, and carbohydrate, and preferably also contains vitamins, minerals, or combinations thereof. The nutritional compositions will comprise at least neutral HMOs, desirably in combination with at least one of protein, fat, vitamins, and minerals, to produce a nutritional composition.

The nutritional compositions may be formulated with sufficient kinds and amounts of nutrients to provide a sole, primary, or supplemental source of nutrition, or to provide a specialized nutritional product for use in individuals afflicted with specific diseases or conditions or with a targeted nutritional benefit as described below.

Examples of nutritional composition forms suitable for use herein include snack and meal replacement products, including those formulated as bars, sticks, cookies or breads or cakes or other baked goods, frozen liquids, candy, breakfast cereals, powders or granulated solids or other particulates, snack chips or bites, frozen or retorted entrees, and so forth. The nutritional composition can also be forms that fall between solid and liquid, such as semi-solid or semi-liquid compositions such as puddings or gels.

Examples of liquid product forms suitable for use herein include snack and meal replacement products, hot or cold beverages, carbonated or non-carbonated beverages, juices or other acidified beverages, milk or soy-based beverages, shakes, coffees, teas, compositions for administration by nasogastric intubation, and so forth. These liquid compositions are most typical formulated as suspensions or emulsions, but can also be formulated in any other suitable form such as clear liquids, substantially clear liquids, liquid gels, and so forth.

The nutritional composition includes one or more ingredients that help satisfy the patients' nutritional requirements. The optional nutrients can provide up to about 1000 kcal of energy per serving or dose, including from about 25 to about 900 kcal, from about 75 to about 700 kcal, from about 150 to about 500 kcal, from about 350 to about 500 kcal, or from about 200 to about 300 kcal.

Most meal replacement products (i.e., bars or liquids) provide calories from fat, carbohydrates, and protein. These products also typically contain vitamins and minerals, because they are intended to be suitable for use as the sole source of nutrition. While these meal replacement products may serve as the sole source of nutrition, they typically don't. Individuals consume these products to replace one or two meals a day, or to provide a healthy snack. The nutritional products of this invention should be construed to include any of these embodiments.

The amount of these nutritional ingredients can vary widely depending upon the targeted patient population (i.e., cancer, HIV/AIDS, arthritis, organoleptic considerations, cultural preferences, use, etc.). As a general non-limiting guideline however, the meal replacement products of this invention will contain the following relative amounts of protein, fat, and carbohydrate (based upon the relative percentage of total calories): a protein component, providing from 5 to 80% of the total caloric content, a carbohydrate component providing from 10 to 70% of the total caloric content, and a lipid component providing from 5 to 50% of the total caloric content.

The meal replacements will contain suitable carbohydrates, lipids and proteins as is known to those skilled in the art of making nutritional formulas. Suitable carbohydrates include, but are not limited to, hydrolyzed, intact, naturally and/or chemically modified starches sourced from corn, tapioca, rice or potato in waxy or non waxy forms; and sugars such as glucose, fructose, lactose, sucrose, maltose, high fructose corn syrup, corn syrup solids, fructooligosaccharides (FOS), and mixtures thereof.

Typically, the FOS comprises from 0 to 5 gm/serving of the meal replacement, preferably from 1 to 5 gm/serving, more preferably from 2 to 4 gm/serving of the meal replacement.

Meal replacements can be manufactured using techniques well known to those skilled in the art. Various processing techniques exist. Typically these techniques include formation of a slurry from one or more solutions, which may contain water and one or more of the following: carbohydrates, proteins, lipids, stabilizers, vitamins and minerals. The neutral HMO is typically added to the carbohydrate slurry prior to the other minerals. The slurry is emulsified, homogenized and cooled. Various other solutions may be added to the slurry before processing, after processing or at both times. The processed formula is then sterilized and may be diluted to be dried to a powder, utilized on a ready-to-feed basis or packaged in a concentrated liquid form. When the resulting formula is meant to be a ready-to-feed liquid or concentrated liquid, an appropriate amount of water would be added before sterilization.

Solid compositions such as bars, cookies, etc. may also be manufactured utilizing techniques known to those skilled in the art. For example, they may be manufactured using cold extrusion technology as is known in the art. To prepare such compositions, typically all of the powdered components will be dry blended together. Such constituents typically include the proteins, vitamin premixes, certain carbohydrates, etc. The fat-soluble components are then blended together and mixed with the powdered premix above. Finally any liquid components are then mixed into the composition, forming a plastic like composition or dough.

The process above is intended to give a plastic mass that can then be shaped, without further physical or chemical changes occurring, by the procedure known as cold forming or extrusion. In this process, the plastic mass is forced at relatively low pressure through a die, which confers the desired shape. The resultant extrudate is then cut off at an appropriate position to give products of the desired weight. If desired the solid product is then coated, to enhance palatability, and packaged for distribution. Typically the package will provide directions for use by the end consumer (i.e., to be consumed by a cancer patient, to help minimize lean muscle loss, etc.)

The solid compositions of the instant invention may also be manufactured through a baked application or heated extrusion to produce cereals, cookies, and crackers. One knowledgeable in the arts would be able to select one of the many manufacturing processes available to produce the desired final product.

As noted above, the neutral HMOs may also be incorporated into juices, non-carbonated beverages, carbonated beverages, electrolyte solutions, flavored waters (hereinafter collectively "beverage"), etc. Methods for producing such beverages are well known in the art. The reader's attention is directed to U.S. Pat. No. 5,792,502, the contents of each which are hereby incorporated by reference. For example, all of the ingredients, including the neutral HMOs, are dissolved in an appropriate volume of water. Flavors, colors, vitamins, etc. are then optionally added. The mixture is then pasteurized, packaged and stored until shipment.

Specific non-limiting examples of product forms suitable for use with the neutral HMO-containing compositions as disclosed herein include, for example, liquid and powdered dietary supplements.

Nutritional Liquids

Nutritional liquids include both concentrated and ready-to-feed nutritional liquids. These nutritional liquids are most typically formulated as suspensions or emulsions, although other liquid forms are within the scope of the present disclosure. Typically, the neutral HMOs may be incorporated into meal replacement beverages such as Ensure®, Glucerna®, etc. The neutral HMOs may be also be incorporated into EAS liquid sports nutritional products. Alternatively, the neutral HMOs may be incorporated into juices, carbonated beverages, bottled water, etc. Additionally, the neutral HMOs may be incorporated into medical nutritionals such as ProSure®, Promote®, Jevity® and Advera® designed to support specific disease states such as cancer, HIV/AIDS, COPD arthritis, etc. Methods for producing any of such food products are well known to those skilled in the art.

When the nutritional product is a concentrated nutritional liquid, the total concentration of neutral HMOs in the concentrated nutritional liquid, by weight of the concentrated nutritional liquid, is from about 0.0002% to about 0.60%, including from about 0.002% to about 0.30%, including from about 0.02% to about 0.20%, and further including from about 0.02% to about 0.06%.

When the nutritional product is a ready-to-feed nutritional liquid, the total concentration of neutral HMOs in the ready-to-feed nutritional liquid, by weight of the ready-to-feed nutritional liquid, is from about 0.0001% to about 0.50%, including from about 0.001% to about 0.15%, including from about 0.01% to about 0.10%, and further including from about 0.01% to about 0.03%.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to about 95% by weight of water, including from about 50% to about 95%, also including from about 60% to about 90%, and also including from about 70% to about 85%, of water by weight of the nutritional emulsions. The nutritional emulsions may have a variety of product densities, but most typically have a density greater than about 1.03 g/mL, including greater than about 1.04 g/mL, including greater than about 1.055 g/mL, including from about 1.06 g/mL to about 1.12 g/mL, and also including from about 1.085 g/mL to about 1.10 g/mL.

The nutritional emulsions may have a caloric density tailored to the nutritional needs of the ultimate user, although in most instances the emulsions comprise generally at least 15 kcal/fl oz (540 kcal/liter), more typically from about 27.5 kcal/fl oz (928 kcal/liter) to about 44 kcal/fl oz (1475-1480 kcal/liter). In some embodiments, the emulsion may have a caloric density of from about 500 kcal/liter to about 3000 kcal/liter, including from about 540 kcal/liter to about 2000 kcal/liter. In some specific embodiments, the emulsion may have a caloric density of 500, or 900 or 1200, or 1500, or 2000 kcal/liter.

The nutritional emulsion may have a pH ranging from about 2.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size is generally at least about 1 mL, or even at least about 2 mL, or even at least about 5 mL, or even at least about 10 mL, or even at least about 25 mL, including ranges from about 1 mL to about 360 mL, including from about 30 mL to about 250 mL, and including from about 60 mL to about 240 mL.

Preferred liquid nutritional compositions include the Ensure® Muscle Health and Ensure® Clinical Strength, both of which are available from Abbott Nutrition (Columbus, Ohio). Non-limiting examples of the composition of Ensure® Clinical Strength (Ensure® CS) are described in Tables 1 and 2 below, with the specific ingredients provided immediately thereafter.

TABLE 1

Product Information

| | UNIT | Ensure ® CS Strawberry, Vanilla per 8 fl oz | Ensure ® CS Chocolate per 8 fl oz |
|---|---|---|---|
| Energy EU | kcal | 350 | 350 |
| Protein | g | 20 | 20 |
| Fat | g | 11 | 11 |
| Linoleic acid | g | 3 | 3 |
| Carbohydrate | g | 44 | 45 |
| Fructooligosaccharide | g | 3 | 2 |
| Sugar | g | 20 | 20 |
| HMO 2'-fucosyllactose | g | 0.05 | 0.12 |
| VITAMINS | | | |
| Vitamin A (Palmitate) | IU | 1000 | 1000 |
| Vitamin A (B-Carotene) | IU | 0 | 0 |
| Vitamin $D_3$ | IU | 160 | 160 |
| Vitamin E | IU | 30 | 30 |
| Vitamin $K_1$ | mcg | 20 | 20 |
| Vitamin C | mg | 60 | 60 |
| Folic Acid | mcg | 200 | 200 |
| Vitamin $B_1$ | mg | 0.38 | 0.38 |
| Vitamin $B_2$ | mg | 0.43 | 0.43 |
| Vitamin $B_6$ | mg | 0.5 | 0.5 |
| Vitamin $B_{12}$ | mcg | 3 | 3 |
| Niacin | mg | 5 | 5 |
| Pantothenate | mg | 2.5 | 2.5 |
| Biotin | mcg | 75 | 75 |
| L-carnitine | mg | 43 | 43 |
| Choline | mg | 83 | 83 |
| MINERALS | | | |
| Sodium | mg | 240 | 240 |
| Potassium | mg | 560 | 630 |
| Chloride | mg | 150 | 150 |
| Calcium | mg | 500 | 500 |
| Phosphorus | mg | 350 | 350 |
| Magnesium | mg | 100 | 100 |
| Iron | mg | 4.5 | 4.5 |
| Zinc | mg | 15 | 15 |
| Manganese | mg | 0.50 | 0.70 |
| Copper | mg | 0.50 | 0.75 |
| Iodine | mcg | 25 | 25 |

TABLE 1-continued

Product Information

| | UNIT | Ensure ® CS Strawberry, Vanilla per 8 fl oz | Ensure ® CS Chocolate per 8 fl oz |
|---|---|---|---|
| Selenium | mcg | 30 | 25 |
| Chromium | mcg | 30 | 40 |
| Molybdenum | mcg | 30 | 30 |

TABLE 2

Product Information

| | UNIT | Ensure ® CS Strawberry, Vanilla per 8 fl oz | Ensure ® CS Chocolate per 8 fl oz |
|---|---|---|---|
| Energy EU | kcal | 350 | 350 |
| Protein | g | 20 | 20 |
| Fat | g | 11 | 11 |
| LCPUFA | mg | 250 | 500 |
| Linoleic acid | g | 3 | 3 |
| Carbohydrate | g | 44 | 45 |
| Fructooligosaccharide | g | 3 | 2 |
| Sugar | g | 20 | 20 |
| HMO 2'-fucosyllactose | g | 0.05 | 0.12 |
| VITAMINS | | | |
| Vitamin A (Palmitate) | IU | 1000 | 1000 |
| Vitamin A (B-Carotene) | IU | 0 | 0 |
| Vitamin $D_3$ | IU | 160 | 160 |
| Vitamin E | IU | 30 | 30 |
| Vitamin $K_1$ | mcg | 20 | 20 |
| Vitamin C | mg | 60 | 60 |
| Carotenoid | mg | 2.4 | 0.00024 |
| Folic Acid | mcg | 200 | 200 |
| Vitamin $B_1$ | mg | 0.38 | 0.38 |
| Vitamin $B_2$ | mg | 0.43 | 0.43 |
| Vitamin $B_6$ | mg | 0.5 | 0.5 |
| Vitamin $B_{12}$ | mcg | 3 | 3 |
| Niacin | mg | 5 | 5 |
| Pantothenate | mg | 2.5 | 2.5 |
| Biotin | mcg | 75 | 75 |
| L-carnitine | mg | 43 | 43 |
| Choline | mg | 83 | 83 |
| MINERALS | | | |
| Sodium | mg | 240 | 240 |
| Potassium | mg | 560 | 630 |
| Chloride | mg | 150 | 150 |
| Calcium | mg | 500 | 500 |
| Phosphorus | mg | 350 | 350 |
| Magnesium | mg | 100 | 100 |
| Iron | mg | 4.5 | 4.5 |
| Zinc | mg | 15 | 15 |
| Manganese | mg | 0.50 | 0.70 |
| Copper | mg | 0.50 | 0.75 |
| Iodine | mcg | 25 | 25 |
| Selenium | mcg | 30 | 25 |
| Chromium | mcg | 30 | 40 |
| Molybdenum | mcg | 30 | 30 |

In a specific embodiment, the nutritional supplement includes Water, Corn syrup, Sucrose, Milk Protein Concentrate, Sodium Caseinate, Canola Oil, Corn Oil, Fructooligosaccharides, Soy Protein Isolate, 2'-fucosyllactose, Whey Protein Concentrate, Potassium Citrate, Natural and Artificial Flavors, Potassium Phosphate, Lecithin, Cellulose Gel, Magnesium Hydroxide, Calcium Carbonate, Ascorbic Acid, Calcium Phosphate, Choline Chloride, Sodium Chloride, Sodium Phosphate, Potassium Hydroxide, Zinc Sulfate, Cellulose Gum, L-Carnitine, Carrageenan, dl-Alpha-Tocopherol Acetate, Dextrose, Ferrous Sulfate, Maltodextrin, Niacinamide, Gellan Gum, Calcium Pantothenate, Citric Acid, Cupric Sulfate, Manganese Sulfate, Chromium Chloride, Thiamine Chloride Hydrochloride, Coconut Oil, Vitamin A Palmitate Pyridoxine Hydrochloride, Riboflavin, Folic Acid, Biotin, Sodium Selenate, Sodium Molybdate, Potassium Iodide, Phylloquinone, Cyanocobalamin, and Vitamin D3.

Nutritional Solids

The nutritional solids may be in any solid form but are typically in the form of flowable or substantially flowable particulate compositions, or at least particulate compositions. Particularly suitable nutritional solid product forms include spray dried, agglomerated and/or dryblended powder compositions. The compositions can easily be scooped and measured with a spoon or similar other device, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

When the nutritional product is a nutritional powder, the total concentration of neutral HMOs, by weight of the nutritional powder, in the nutritional powder is from about 0.0005% to about 5%, including from about 0.01% to about 1%.

The nutritional powders may be reconstituted with water prior to use to a caloric density tailored to the nutritional needs of the ultimate user, although in most instances the powders are reconstituted with water to form compositions comprising generally at least 15 kcal/fl oz (540 kcal/liter), more typically from about 27.5 kcal/fl oz (928 kcal/liter) to about 44 kcal/fl oz (1475-1480 kcal/liter). In some embodiments, the emulsion may have a caloric density of from about 500 kcal/liter to about 3000 kcal/liter, including from about 540 kcal/liter to about 2000 kcal/liter. In some specific embodiments, the emulsion may have a caloric density of 500, or 900 or 1200, or 1500, or 2000 kcal/liter.

In a further embodiment, the neutral HMOs may be incorporated into beverages, bars, cookies, etc. that have been specifically designed to enhance the palatability of the neutral HMOs and increase the selection of alternative forms, thereby enhancing patient/consumer acceptance. The neutral HMOs may be incorporated into meal replacement or snack bars such as Glucerna® bars, ZonePerfect® bars and EAS® Sports Nutrition bars, etc. Methods for producing any of such food products are well known to those skilled in the art. The following discussion is intended to illustrate such food products and their preparation.

Where the nutritional composition is provided in the form of a bar, the nutritional bar may include at least one neutral human milk oligosaccharide in an amount of from about 0.01 mg/bar to about 10 g/bar, including from about 0.01 mg/bar to less than 2 g/bar, and also including from 0.1 mg/bar to about 10 g/bar, including from about 0.1 mg/bar to less than 2 g/bar.

Preferred bar nutritional compositions include the Glucerna® Hunger Smart Bar, Glucerna® Snack Bar, Glucerna® Meal Replacement Bar, ZonePerfect® Bar, EAS® Lean 15™ Bar and EAS® Myoplex 30™ Bar, all of which are available from Abbott Nutrition (Columbus, Ohio). An example composition for the Glucerna® Hunger Smart Chocolate Chip Snack Bar is described in Table 3 below, with the specific ingredients provided immediately thereafter.

TABLE 3

Glucerna Hunger Smart Product Example Information
Serving size - 1 bar

| Amount per serving | | | % DV |
|---|---|---|---|
| Calories | 140 | | |
| Calories from fat | 40 | | |
| Total fat | 4.5 | g | 7% |
| Saturated fat | 2.5 | g | 13% |
| n3-LCPUFA | 0.2 | g | |
| Trans fat | 0 | g | |
| Cholesterol | 0 | mg | 0% |
| Sodium | 180 | mg | 8% |
| Potassium | 70 | mg | 2% |
| Total Carbohydrate | 20 | g | 7% |
| Dietary fiber | 3 | g | 12% |
| Sugars | 5 | g | |
| 2-fucosyllactose | 0.12 | g | |
| Sugar Alcohols | 8 | g | |
| Protein | 10 | g | 20% |
| Vitamin A | | | 15% |
| Calcium | | | 15% |
| Vitamin E | | | 100% |
| Vitamin C | | | 20% |
| Iron | | | 10% |
| Chromium | | | 30% |

In a specific example embodiment of the invention, the Glucerna® Hunger Smart Chocolate Chip Snack Bar shown above includes: soy protein crisps, chocolate flavored coating fruit juice and grain dextrins, marshmallow binder, fructose liquid, chocolate flavored chips, soy protein isolate, corn maltodextrin, short chain fructooligosaccharides, 2-fucosyllactose, glycerine, high oleic safflower oil, and a chocolate layer.

Methods of Manufacture

The nutritional compositions of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the nutritional compositions described herein.

The nutritional compositions of the present disclosure can therefore be prepared by any of a variety of known or otherwise effective formulation or manufacturing methods. In one suitable manufacturing process, for example, at least three separate slurries are prepared, including a protein-in-fat (PIF) slurry, a carbohydrate-mineral (CHO-MN) slurry, and a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., neutral HMOs, fructooligosaccharide, sucrose, corn syrup, etc.). The PIW slurry is then formed by mixing with heat and agitation the remaining protein, if any.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

The nutritional solid, such as a spray dried nutritional powder or drymixed nutritional powder, may be prepared by any collection of known or otherwise effective technique, suitable for making and formulating a nutritional powder.

For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, drymixing, or otherwise adding additional nutritional ingredients, including any one or more of the ingredients described herein, to the spray dried nutritional powder.

Other suitable methods for making nutritional products are described, for example, in U.S. Pat. No. 6,365,218 (Borschel et al.), U.S. Pat. No. 6,589,576 (Borschel et al.), U.S. Pat. No. 6,306,908 (Carlson et al.), U.S. Patent Application 20030118703 A1 (Nguyen et al.), which descriptions are incorporated herein by reference to the extent that they are consistent herewith. Methods for making nutritional bars are described in U.S. Pat. No. 6,248,375, and the descriptions are incorporated herein by reference to the extent that they are consistent herewith.

Methods of Use

The nutritional compositions as described herein can be used to address one or more of the diseases or conditions discussed herein, or can be used to provide one or more of the benefits described herein, to adults and elderly individuals. The adult or elderly individual utilizing the nutritional compositions described herein may actually have or be afflicted with the disease or condition described, or may be susceptible to, or at risk of, getting the disease or condition (that is, may not actually yet have the disease or condition, but is at elevated risk as compared to the general population for getting it due to certain conditions, family history, etc.) Whether adult or elderly individual actually has the disease or condition, or is at risk or susceptible to the disease or condition, the adult or elderly individual is classified herein as "in need of" assistance in dealing with and combating the disease or condition. For example, the adult or elderly individual may actually have respiratory inflammation or may be at risk of getting respiratory inflammation (susceptible to getting respiratory inflammation) due to family history or other medical conditions, for example. Whether the adult or elderly individual actually has the disease or condition, or is only at risk or susceptible to getting the disease or condition, it is within the scope of the present disclosure to assist the adult or elderly individual with the nutritional compositions described herein.

Also, 2'FL, alone or in combination with another neutral HMO (e.g., 3FL) is appropriate for use in pediatric, adult product and elderly populations where a decrease in inflammation is desired. Populations with need include those: in the midst of microbial infection (respiratory or gastrointestinal infection; sepsis; periodontitis; at risk of NEC; at risk of vascular inflammation; at risk of increased PNC formation (diabetic women, ischemic patients, active sickle cell disease); at risk of chronic inflammation (elderly, allergy/asthma, IBD, NEC).

Based on the foregoing, because some of the method embodiments of the present disclosure are directed to specific subsets or subclasses of identified individuals (that is, the subset or subclass of individuals "in need" of assistance in addressing one or more specific diseases or specific conditions noted herein), not all adults or elderly individuals will fall within the subset or subclass of adults or elderly individuals as described herein for certain diseases or conditions.

The nutritional compositions as described herein comprise neutral HMOs, alone or in combination with one or more additional components, to provide a nutritional source for reducing inflammation, such as respiratory inflammation (e.g., respiratory syncytial virus-induced inflammation), enteric inflammation, nasopharyngeal inflammation and systemic inflammation.

Further, the use of neutral HMOs in nutritional compositions can reduce the growth of respiratory viruses (e.g., RSV, human parainfluenza virus type 2, and influenza A virus), and thus, reduce viral-induced upper respiratory infections.

The use of the nutritional compositions of the present disclosure also functions as an immune modulator, thereby reducing inflammation induced by infection in adults and the elderly population, such as respiratory virus-induced infection, and particularly, RSV-induced inflammation, and other infection-mediated inflammatory diseases.

When used in combination with LCPUFAs and/or antioxidants, and particularly, with carotenoids, the neutral HMOs can reduce oxidative stress, which is a metabolic condition in which there is an increased production and accumulation of oxidized biomolecules such as lipid peroxides and their catabolites, protein carbonyls, and oxidatively damaged DNA. The outcomes of oxidative stress range from unwanted changes in metabolism to inflammation and cell and tissue death. Accordingly, by reducing the incidence of unregulated inflammation and oxidation, damage to the tissue lining and cell death is reduced, further reducing the incidence of inflammatory diseases.

In addition to the benefits discussed above, it has been discovered that nutritional products including neutral HMOs can modulate production of monocyte-derived cytokines, even in the absence of a virus. This production results in improved immunity to further minimize microbial infection and reduce the growth of viruses. In one specific embodiment, monocyte-derived cytokines produced by administration of the nutritional compositions of the present disclosure include, for example, interleukin-10, interleukin-8, interleukin-1α, interleukin-1β, interleukin-1ra, and combinations thereof.

Another benefit of utilizing neutral HMOs in nutritional compositions is that it has been discovered that neutral HMOs modulate the production of IP-10, which is a chemokine that plays an important role in the inflammatory response to viral infection. Specifically, a positive correlation exists between RSV clinical infection severity and serum IP-10 levels. Accordingly, a decrease in IP-10 signals a decrease in severity of RSV infection. In one specific embodiment, IP-10 production is reduced to the level found in uninfected controls.

Along with reducing IP-10, neutral HMOs have been found to reduce platelet-neutrophil complex (PNC) formation, which is present in human blood and consists of up to 25% of unstimulated neutrophils. As PNCs are present in aggregates, they have a greater capacity to initiate inflammatory processes and can increase the production of reactive oxygen species. Accordingly, a decrease in PNC formation can lead to reduced oxidative stress and inflammation.

EXAMPLES

The following examples illustrate specific embodiments, features, or both of the nutritional compositions of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified compositions are shelf stable nutritional compositions prepared in accordance with the manufacturing methods described herein, such that each exemplified composition, unless otherwise specified, includes an aseptically processed embodiment and a retort packaged embodiment.

Example 1

Data was generated using an in vitro simulation of PNC formation with a 15 minute ingredient incubation period.

Neutral HMOs

Results shown in FIG. 1 demonstrate that 2'FL alone at a concentration of 125 µg/mL, as well as the FL Mix (70% 2'FL:30% 3FL=87.5 µg 2'FL/mL: 37.5 µg 3FL/mL) significantly reduces PNC formation. The data (n=2-3 individuals) in FIG. 1 unexpectedly shows that 2'FL alone or as part of the FL mix (70% 2'FL:30% 3FL=87.5 ug 2'FL/mL: 37.5 ug 3FL/mL) decreased inflammation by decreasing PNC formation. This is unexpected as published information indicates that pooled neutral HMOs (which would include 2'FL and 3FL) do not decrease PNC formation.

Acidic HMOs

Our data also show that the individual acidic HMOs 3'SL and 6'SL do not decrease PNC formation; and neither does sialic acid (SL). This is unexpected in light of prior data showing that pooled acidic HMOs decrease PNC formation.

Example 2

Neutral HMOs 2'FL and LNnT Decrease PNC Formation

When selected data from this PNC experiment is detailed by donor and ingredient as shown in Table 4, we see that 2'FL decreased PNC formation in all 3 individuals tested. It is also evident that LNnT decreased PNC formation in 2 out of the 3 subjects tested. Test concentration was 125 µg/mL for all ingredients tested. Cells were incubated with test ingredients or medium alone (ADP) for 15 minutes. ADP (10 µM) was added to each tube and incubated for 15 minutes. The ADP alone contained no test ingredient. Data is expressed as % CD11b+CD42a+ in the tested conditions as a percent of those events that were CD11b+CD42a+ under ADP stimulation. Average response for 2'FL and LNnT showed these ingredients have the lowest % CD11b+CD42a+ values, indicating the greatest decrease in PNC formation.

TABLE 4

% CD11b+CD42a+ in the tested condition as a percent of those events that were CD11b+CD42a+ under ADP stimulation:

|  | sLeX | 2FL | 3FL | 3SL | 6SL | iHMO | LNnT | ADP (10 uM) |
|---|---|---|---|---|---|---|---|---|
| subject 1 | 91.1 | 87.8 | 80.8 | 91.3 | 90.1 | 133.0 | 102.3 | 100.0 |
| subject 2 | 68.8 | 62.1 | 64.3 | 89.3 | 59.8 | 76.5 | 82.9 | 100.0 |
| subject 3 |  | 50.7 | 104.1 | 117.1 | 132.8 | 101.5 | 41.1 | 100.0 |
| average | 80.0 | 66.9 | 83.1 | 99.2 | 94.2 | 103.7 | 75.4 | 100.0 |
| SD | 15.8 | 19.0 | 20.0 | 15.5 | 36.7 | 28.3 | 31.3 | 0.0 |
| SEM | 7.9 | 6.3 | 6.7 | 5.2 | 12.2 | 9.4 | 10.4 | 0.0 |

Example 3

Example 3 illustrates an emulsion of the present disclosure, including HMOs, the ingredients of which are listed in the table below. All ingredient amounts are listed as pound per approximately 1000 pounds batch of product, unless otherwise specified.

| Ingredient | lb/1000 lbs |
|---|---|
| Water | Q.S. |
| Milk Protein Concentrate | 66.6 |
| Sucrose | 51.3 |
| Maltodextrin | 36.0 |
| Soy Protein Isolate | 15.9 |
| Soy Oil | 12.5 |
| HMO | 0.2 |
| Corn Oil | 5.89 |
| Potassium Citrate | 4.48 |
| Canola Oil | 4.17 |
| Micronized-Tricalcium Phosphate | 2.40 |
| Sodium Citrate | 2.02 |
| Magnesium Chloride | 1.88 |
| Magnesium Phosphate Dibasic | 1.55 |
| Flavoring Agent | 1.50 |
| LCPUFA | 1.05 |
| Sodium Chloride | 1.00 |
| Soy Lecithin | 0.982 |
| Choline Chloride | 0.540 |
| Ascorbic Acid | 0.420 |
| Gellan Gum | 0.400 |
| UTM/TM Premix | 0.301 |
| Zinc Sulfate, Monohydrate | 0.068450 |
| Ferrous Sulfate, Dried | 0.053460 |
| Manganese Sulfate, Monohydrate | 0.016990 |
| Cupric Sulfate, Pentahydrate | 0.009248 |
| Chromium Chloride, Hexahydrate | 0.000573 |
| Sodium Molybdate, Dihydrate | 0.000463 |
| Sodium Selencate, Anhydrous | 0.000191 |
| 45% KOH | 0.250 |
| Potassium Hydroxide | 0.1126 |
| Carrageenan | 0.350 |
| Water Soluble Vitamin Premix | 0.0727 |
| Niacinamide | 0.02726 |
| Calcium Pantothenate | 0.01763 |
| Thiamine Chloride Hydrochloride | 0.004504 |
| Pyridoxine Hydrochloride | 0.004337 |
| Riboflavin | 0.003519 |
| Folic Acid | 0.000611 |
| Biotin | 0.0005311 |
| Cyanoconbalamin | 0.00001203 |
| Vitamin DEK Premix | 0.0644 |
| dl-Alpha-Tocopheryl Acetate | 0.05392 |
| Phylloquinone | 0.00008012 |
| Vitamin D3 | 0.00001308 |
| Vitamin A Palmitate | 0.00825 |
| Potassium Iodide | 0.000206 |

Example 4

Example 4 illustrates an emulsion of the present disclosure, including HMOs, the ingredients of which are listed in the table below. All ingredient amounts are listed as pound per approximately 1000 pounds batch of product, unless otherwise specified.

| Ingredient | lb/1000 lbs |
|---|---|
| Water | Q.S. |
| Milk Protein Concentrate | 61.6 |
| Sucrose | 51.4 |
| Maltodextrin | 36.0 |
| Soy Protein Isolate | 14.7 |
| Soy Oil | 10.9 |
| Whey Protein Phospholipid Concentrate | 9.47 |
| HMO | 0.5 |
| Corn Oil | 5.19 |
| Potassium Citrate | 4.48 |
| Canola Oil | 3.68 |
| Micronized-Tricalcium Phosphate | 2.40 |
| Sodium Citrate | 2.02 |
| Magnesium Chloride | 1.88 |
| Magnesium Phosphate Dibasic | 1.55 |
| Flavoring Agent | 1.50 |
| LCPUFA | 1.05 |
| Sodium Chloride | 1.00 |
| Soy Lecithin | 0.865 |
| Choline Chloride | 0.540 |
| Ascorbic Acid | 0.420 |
| UTM/TM Premix | 0.301 |
| Zinc Sulfate, Monohydrate | 0.068450 |
| Ferrous Sulfate, Dried | 0.053460 |
| Manganese Sulfate, Monohydrate | 0.016990 |
| Cupric Sulfate, Pentahydrate | 0.009248 |
| Carotenoid | 0.000001 |
| Chromium Chloride, Hexahydrate | 0.000573 |
| Sodium Molybdate, Dihydrate | 0.000463 |
| Sodium Selencate, Anhydrous | 0.000191 |
| 45% KOH | 0.250 |
| Potassium Hydroxide | 0.1126 |
| Carrageenan | 0.350 |
| Water Soluble Vitamin Premix | 0.0727 |
| Niacinamide | 0.02726 |
| Calcium Pantothenate | 0.01763 |
| Thiamine Chloride Hydrochloride | 0.004504 |
| Pyridoxine Hydrochloride | 0.004337 |
| Riboflavin | 0.003519 |
| Folic Acid | 0.000611 |
| Biotin | 0.0005311 |
| Cyanoconbalamin | 0.00001203 |
| Vitamin DEK Premix | 0.0644 |
| dl-Alpha-Tocopheryl Acetate | 0.05392 |
| Phylloquinone | 0.00008012 |
| Vitamin D3 | 0.00001308 |
| Vitamin A Palmitate | 0.00825 |
| Potassium Iodide | 0.000206 |

Example 5

Example 5 illustrates an emulsion of the present disclosure, including HMOs, the ingredients of which are listed in the table below. All ingredient amounts are listed as pound per approximately 1000 pounds batch of product, unless otherwise specified.

| Ingredient | lb/1000 lbs |
|---|---|
| Water | Q.S. |
| Milk Protein Concentrate | 66.6 |
| Sucrose | 51.5 |
| Maltodextrin | 36.2 |
| Soy Protein Isolate | 15.9 |
| Soy Oil | 11.4 |
| HMO | 1.0 |
| Corn Oil | 5.89 |
| Potassium Citrate | 4.48 |
| Canola Oil | 4.17 |
| Micronized-Tricalcium Phosphate | 2.40 |
| LCPUFA | 2.11 |
| Sodium Citrate | 2.02 |
| Magnesium Chloride | 1.88 |
| Magnesium Phosphate Dibasic | 1.55 |
| Flavoring Agent | 1.50 |
| Sodium Chloride | 1.00 |
| Soy Lecithin | 0.865 |
| Choline Chloride | 0.540 |
| Ascorbic Acid | 0.420 |
| UTM/TM Premix | 0.301 |
| Zinc Sulfate, Monohydrate | 0.068450 |
| Ferrous Sulfate, Dried | 0.053460 |
| Manganese Sulfate, Monohydrate | 0.016990 |
| Cupric Sulfate, Pentahydrate | 0.009248 |
| Chromium Chloride, Hexahydrate | 0.000573 |
| Sodium Molybdate, Dihydrate | 0.000463 |
| Sodium Selencate, Anhydrous | 0.000191 |
| 45% KOH | 0.250 |
| Potassium Hydroxide | 0.1126 |
| Carrageenan | 0.350 |
| Water Soluble Vitamin Premix | 0.0727 |
| Niacinamide | 0.02726 |
| Calcium Pantothenate | 0.01763 |
| Thiamine Chloride Hydrochloride | 0.004504 |
| Pyridoxine Hydrochloride | 0.004337 |
| Riboflavin | 0.003519 |
| Folic Acid | 0.000611 |
| Biotin | 0.0005311 |
| Cyanoconbalamin | 0.00001203 |
| Vitamin DEK Premix | 0.0644 |
| dl-Alpha-Tocopheryl Acetate | 0.05392 |
| Phylloquinone | 0.00008012 |
| Vitamin D3 | 0.00001308 |
| Vitamin A Palmitate | 0.00825 |
| Potassium Iodide | 0.000206 |

Example 6

Example 6 illustrates a substantially clear nutritional liquid of the present disclosure, including HMOs, the ingredients of which are listed in the table below. This liquid has a pH of between 2.9 and 4.0 and remains physically stable over a shelf life of about 18 months. All ingredient amounts are listed as pound per approximately 1000 pounds batch of product, unless otherwise specified.

| Ingredient | lb/1000 lbs |
|---|---|
| Water | Q.S. |
| Sucrose | 78.1 |
| Whey Protein Isolate | 39.5 |
| Phosphoric Acid | 1.8 |
| Citric Acid | 1.3 |
| Acid Blend | 38.7 |
| Citric Acid | 1.9 |
| Phosphoric Acid | 1.9 |
| Maltodextrin | 20.1 |
| HMO | 0.3 |
| Glycine | 2.56 |
| Citric Acid | 2.00 |
| Flavoring Agent | 2.00 |
| Liquid Sucralose (25%) | 0.300 |
| Sucralose | 0.0750 |
| UTM/TM premix | 0.230 |
| Zinc Sulfate, monohydrate | 0.0521 |
| Ferrous sulfate, dried | 0.0408 |
| Citric Acid, anhydrous | 0.0142 |
| Manganese Sulfate, monohydrate | 0.0130 |
| Copper Sulfate, pentahydrate | 0.00710 |
| Chromium Chloride, hexahydrate | 0.000430 |
| Sodium Molybdate, dihydrate | 0.000339 |
| Sodium Selenate, anhydrous | 0.000146 |
| Water Dispersible ADEK premix | 0.178 |
| dl-Alpha-Tocopheryl Acetate | 0.0454 |
| Vitamin A Palmitate | 0.00421 |
| Phylloquinone | 0.000127 |
| Vitamin D3 | 0.0000231 |
| Carotenoid | 0.01 |
| Acesulfame Potassium | 0.110 |
| 10% DMPS Anti-foam (Processing Aid) | 0.0600 |
| Dimethylpolysiloxane | 0.0006 |
| Water Soluble Vitamin premix | 0.03790 |
| Niacinamide | 0.0142 |
| d-Calcium pantothenate | 0.00920 |
| Thiamine chloride hydrochloride | 0.00240 |
| Pyridoxine hydrochloride | 0.00230 |
| Riboflavin | 0.00180 |
| Folic Acid | 0.000350 |
| Biotin | 0.000277 |
| Cyanocobalamin | 0.00000630 |
| Coloring Agent | 0.00700 |
| Folic Acid, USP | 0.00337 |
| Potassium Iodide | 0.000204 |

Example 7

Example 7 illustrates a substantially clear nutritional liquid of the present disclosure, including HMOs, the ingredients of which are listed in the table below. This liquid has a pH of between 2.9 and 4.0 and remains physically stable over a shelf life of about 18 months. All ingredient amounts are listed as pound per approximately 1000 pounds batch of product, unless otherwise specified.

| Ingredient | lb/1000 lbs |
|---|---|
| Water | Q.S. |
| Sucrose | 78.1 |
| Whey Protein Isolate | 39.5 |
| Phosphoric Acid | 1.8 |
| Citric Acid | 1.3 |
| Acid Blend | 38.7 |
| Citric Acid | 1.9 |
| Phosphoric Acid | 1.9 |
| Maltrodextrin | 20.1 |
| HMO | 0.6 |
| Taurine | 2.56 |
| Citric Acid | 2.00 |
| Flavoring Agent | 2.00 |
| Liquid Sucralose (25%) | 0.300 |
| Sucralose | 0.0750 |
| Carotenoid | 0.01 |
| UTM/TM premix | 0.230 |
| Zinc Sulfate, monohydrate | 0.0521 |
| Ferrous sulfate, dried | 0.0408 |
| Citric Acid, anhydrous | 0.0142 |
| Manganese Sulfate, monohydrate | 0.0130 |
| Copper Sulfate, pentahydrate | 0.00710 |
| Chromium Chloride, hexahydrate | 0.000430 |

-continued

| Ingredient | lb/1000 lbs |
|---|---|
| Sodium Molybdate, dihydrate | 0.000339 |
| Sodium Selenate, anhydrous | 0.000146 |
| Water Dispersible ADEK premix | 0.178 |
| dl-Alpha-Tocopheryl Acetate | 0.0454 |
| Vitamin A Palmitate | 0.00421 |
| Phylloquinone | 0.000127 |
| Vitamin D3 | 0.0000231 |
| Acesulfame Potassium | 0.110 |
| 10% DMPS Anti-foam (Processing Aid) | 0.0600 |
| Dimethylpolysiloxane | 0.0006 |
| Water Soluble Vitamin premix | 0.03790 |
| Niacinamide | 0.0142 |
| d-Calcium pantothenate | 0.00920 |
| Thiamine chloride hydrochloride | 0.00240 |
| Pyridoxine hydrochloride | 0.00230 |
| Riboflavin | 0.00180 |
| Folic Acid | 0.000350 |
| Biotin | 0.000277 |
| Cyanocobalamin | 0.00000630 |
| Coloring Agent | 0.00700 |
| Folic Acid, USP | 0.00337 |
| Potassium Iodide | 0.000204 |

While the disclosure describes several examples and embodiments in detail, the description is given solely for the purpose of illustration and is not to be construed so as to limit the disclosure. Many variations from the examples and embodiments described herein are possible without departing from the spirit and scope of the disclosure.

What is claimed is:

1. A method of reducing platelet neutrophil complex concentration in an adult or elderly individual in need thereof, the method comprising administering a synthetic nutritional composition comprising a human milk oligosaccharide selected from the group consisting of 2'-fucosyllactose, 3-fucosyllactose, and lacto-N-neotetraose, wherein the human milk oligosaccharide is present in a concentration of from about 0.001 mg/mL to less than about 2 mg/mL.

2. The method of claim 1, wherein the at least one human milk oligosaccharide is 2'-fucosyllactose.

3. The method of claim 1, wherein the at least one human milk oligosaccharide is lacto-N-neotetraose (LNnT).

4. The method of claim 1, wherein the at least one human milk oligosaccharide is 3-fucosyllactose.

5. The method of claim 1, wherein the composition additionally comprises a long chain polyunsaturated fatty acid in a concentration that does not exceed about 5% of total fat content in the nutritional composition.

6. The method of claim 1, wherein the composition additionally comprises a carotenoid, in a concentration from about 0.001 µg/mL to about 10 µg/mL.

* * * * *